United States Patent
Bowen et al.

(10) Patent No.: US 11,565,059 B2
(45) Date of Patent: Jan. 31, 2023

(54) MASS OUTPUT CONTROLLED VAPORIZER

(71) Applicant: JUUL Labs, Inc., San Francisco, CA (US)

(72) Inventors: Adam Bowen, San Mateo, CA (US); Ariel Atkins, San Francisco, CA (US)

(73) Assignee: JUUL Labs, Inc., San Francisco, CA (US)

( * ) Notice: Subject to any disclaimer, the term of this patent is extended or adjusted under 35 U.S.C. 154(b) by 874 days.

(21) Appl. No.: 16/287,667

(22) Filed: Feb. 27, 2019

(65) Prior Publication Data

US 2019/0261689 A1    Aug. 29, 2019

Related U.S. Application Data

(60) Provisional application No. 62/636,086, filed on Feb. 27, 2018.

(51) Int. Cl.
*A61M 15/06* (2006.01)
*H05B 1/02* (2006.01)
(Continued)

(52) U.S. Cl.
CPC ............. *A61M 15/06* (2013.01); *A24F 40/50* (2020.01); *A61M 11/042* (2014.02); *H05B 1/0283* (2013.01); *A24F 40/10* (2020.01); *A61M 15/0025* (2014.02); *A61M 2016/0027* (2013.01); *A61M 2016/0039* (2013.01); *A61M 2205/332* (2013.01); *A61M 2205/3317* (2013.01); *A61M 2205/3334* (2013.01);
(Continued)

(58) Field of Classification Search
CPC ..................................................... A24F 47/008
See application file for complete search history.

(56) References Cited

U.S. PATENT DOCUMENTS 7,143,766 B2    12/2006   Schuster et al.
7,173,222 B2    2/2007    Cox et al.
(Continued)

FOREIGN PATENT DOCUMENTS

CN              1633247 A      6/2005
CN              104571191 B    1/2018
(Continued)

*Primary Examiner* — Nathaniel Herzfeld
(74) *Attorney, Agent, or Firm* — Mintz Levin Cohn Ferris Glovsky and Popeo, P.C.

(57) ABSTRACT

A vaporizer device includes a resistive heating element; circuitry configured to control delivery of electrical power to the resistive heating element from a power source; and a controller configured to perform operations including: receiving inputs representative of a power delivery to the resistive heating element, a temperature of the resistive heating element, and/or a flow rate of air past the resistive heating element; predicting, using the received inputs, an amount of evaporation of the vaporizable material at the resistive heating element; and controlling the power delivery to the resistive heating element in response to the predicted amount of evaporation of the vaporizable material, the controlling including increasing or decreasing an instantaneous power delivery to the heating element such that a target aerosol yield is produced. Related devices, systems, methods, and articles are also described.

20 Claims, 5 Drawing Sheets

(51) Int. Cl.
  *A61M 11/04* (2006.01)
  *A24F 40/50* (2020.01)
  *A61M 16/00* (2006.01)
  *A61M 15/00* (2006.01)
  *A24F 40/10* (2020.01)

(52) U.S. Cl.
  CPC .............. *A61M 2205/3368* (2013.01); *A61M 2205/3553* (2013.01); *A61M 2205/3653* (2013.01); *A61M 2205/502* (2013.01); *A61M 2205/581* (2013.01); *A61M 2205/582* (2013.01); *A61M 2205/587* (2013.01); *A61M 2205/8212* (2013.01)

(56) References Cited

U.S. PATENT DOCUMENTS

| | | | |
|---|---|---|---|
| 8,371,310 B2 | 2/2013 | Brenneise | |
| 9,399,110 B2 | 7/2016 | Goodman et al. | |
| 9,814,263 B2 | 11/2017 | Degoumois et al. | |
| 9,999,250 B2 | 6/2018 | Minskoff et al. | |
| 10,058,122 B2 | 8/2018 | Steingraber et al. | |
| 10,058,129 B2 | 8/2018 | Monsees et al. | |
| 10,131,532 B2 | 11/2018 | Murison et al. | |
| 10,512,282 B2 | 12/2019 | Bowen et al. | |
| 2003/0154991 A1 | 8/2003 | Fournier et al. | |
| 2011/0167895 A1* | 7/2011 | Hingley | A61L 2/26 73/30.01 |
| 2012/0048266 A1 | 3/2012 | Alelov | |
| 2013/0104916 A1* | 5/2013 | Bellinger | A61M 15/06 131/328 |
| 2013/0319435 A1 | 12/2013 | Flick | |
| 2014/0020693 A1* | 1/2014 | Cochand | A61M 15/06 131/273 |
| 2014/0041658 A1 | 2/2014 | Goodman et al. | |
| 2014/0096781 A1 | 4/2014 | Sears et al. | |
| 2014/0096782 A1 | 4/2014 | Ampolini et al. | |
| 2014/0299141 A1 | 10/2014 | Flick | |
| 2014/0321837 A1 | 10/2014 | Flick | |
| 2014/0338685 A1 | 11/2014 | Amir | |
| 2014/0345633 A1 | 11/2014 | Talon et al. | |
| 2014/0352690 A1* | 12/2014 | Kolb | A61M 11/00 128/200.14 |
| 2015/0173419 A1* | 6/2015 | Tu | A24F 40/46 131/329 |
| 2015/0272220 A1 | 10/2015 | Spinka et al. | |
| 2015/0272222 A1 | 10/2015 | Spinka et al. | |
| 2015/0359263 A1 | 12/2015 | Bellinger | |
| 2015/0359264 A1 | 12/2015 | Fernando et al. | |
| 2016/0143361 A1 | 5/2016 | Juster et al. | |
| 2016/0157524 A1* | 6/2016 | Bowen | A61M 11/042 128/200.14 |
| 2016/0174611 A1 | 6/2016 | Monsees et al. | |
| 2016/0255878 A1* | 9/2016 | Huang | A24F 40/485 |
| 2016/0295922 A1 | 10/2016 | John et al. | |
| 2017/0020195 A1 | 1/2017 | Cameron | |
| 2017/0045994 A1 | 2/2017 | Murison et al. | |
| 2017/0119052 A1 | 5/2017 | Williams et al. | |
| 2017/0135406 A1 | 5/2017 | Reevell | |
| 2017/0150758 A1 | 6/2017 | Fernando et al. | |
| 2017/0156399 A1 | 6/2017 | Freeman et al. | |
| 2017/0188626 A1 | 7/2017 | Davis et al. | |
| 2017/0245551 A1 | 8/2017 | Reevell | |
| 2017/0360093 A1 | 12/2017 | Fernando | |
| 2018/0042306 A1 | 2/2018 | Atkins et al. | |
| 2018/0043114 A1 | 2/2018 | Bowen et al. | |
| 2018/0070641 A1 | 3/2018 | Batista et al. | |
| 2018/0077967 A1 | 3/2018 | Hatton et al. | |
| 2018/0098574 A1 | 4/2018 | Sur et al. | |
| 2018/0184722 A1 | 7/2018 | Murison et al. | |
| 2018/0296777 A1 | 10/2018 | Terry et al. | |
| 2018/0303169 A1 | 10/2018 | Sears et al. | |
| 2019/0158938 A1 | 5/2019 | Bowen et al. | |
| 2019/0159519 A1 | 5/2019 | Bowen et al. | |
| 2019/0380388 A1 | 12/2019 | Amorde et al. | |
| 2019/0387796 A1 | 12/2019 | Cohen | |
| 2020/0000143 A1 | 1/2020 | Anderson et al. | |
| 2020/0046033 A1 | 2/2020 | Robert et al. | |
| 2020/0120991 A1 | 4/2020 | Hatton et al. | |

FOREIGN PATENT DOCUMENTS

| | | |
|---|---|---|
| DE | 202013105420 U1 | 4/2014 |
| JP | 2001161819 A | 6/2001 |
| KR | 20190057399 A | 5/2019 |
| WO | WO-2008015918 A1 | 2/2008 |
| WO | WO-2015091258 A1 | 6/2015 |
| WO | WO-2016145634 A1 | 9/2016 |
| WO | WO-2016168986 A1 | 10/2016 |
| WO | WO-2016201911 A1 | 12/2016 |
| WO | WO-2017057286 A1 | 4/2017 |
| WO | WO-2017084818 A1 | 5/2017 |
| WO | WO-2017141017 A1 | 8/2017 |
| WO | WO-2017207416 A1 | 12/2017 |
| WO | WO-2017207419 A1 | 12/2017 |
| WO | WO-2019104227 A1 | 5/2019 |
| WO | WO-2019126805 A1 | 6/2019 |
| WO | WO-2019173923 A1 | 9/2019 |
| WO | WO-2020020788 A1 | 1/2020 |
| WO | WO-2020023547 A1 | 1/2020 |

\* cited by examiner

MASS OUTPUT CONTROLLED VAPORIZER

CROSS-REFERENCE TO RELATED APPLICATION

This application claims priority to U.S. Provisional Patent Application No. 62/636,086 filed Feb. 27, 2018, and entitled "Mass Output Controlled Vaporizer", the entire contents of which is hereby expressly incorporated herein by reference.

TECHNICAL FIELD

The subject matter described herein relates to mass output control for a vaporizer device.

BACKGROUND

Vaporizer devices, which include and/or may be referred to as electronic inhalable aerosol devices, vaporization devices, electronic vaping devices, and/or electronic aerosol devices, typically utilize a vaporizable material that is vaporized to create an aerosol vapor capable of delivering an active ingredient to a user. Maintaining some degree of control of the temperature of the resistive heater is generally desirable, for example, to avoid overheating of the vaporizable material, to ensure that sufficient heat is available to form the aerosol, to maintain longer battery life of the vaporizer device, and the like.

SUMMARY

Implementations of the current subject matter relate to approaches for controlling an aerosol output rate provided by a vaporizer device.

In one aspect, a vaporizer device includes a heating element and circuitry to control delivery of electrical power to the heating element from a power source. A controller implements a control law based on received inputs representative of one or more of a power delivery to the resistive heating element, a temperature of the resistive heating element, and/or a flow rate of air past the resistive heating element. The inputs are used to predict an amount of evaporation of vaporizable material at the heating element. In response to the predicted amount of evaporation of the vaporizable material, power delivery to the heating element is controlled by increasing or decreasing the power delivery to the heater to reach a target aerosol yield.

In another aspect, a vaporizer device includes a resistive heating element; circuitry configured to control delivery of electrical power to the resistive heating element from a power source, the resistive heating element configured to provide heat to a vaporizable material to cause vaporization of the vaporizable material into a flowing air stream to form an entrained aerosol; and a controller configured to perform operations including: receiving inputs representative of a power delivery to the resistive heating element, a temperature of the resistive heating element, and/or a flow rate of air past the resistive heating element; predicting, using the received inputs, an amount of evaporation of the vaporizable material at the resistive heating element; and controlling the power delivery to the resistive heating element in response to the predicted amount of evaporation of the vaporizable material, the controlling including increasing or decreasing an instantaneous power delivery to the heating element such that a target aerosol yield is produced.

One or more of the following features can be included in any feasible combination. For example, the received input representative of the flow rate of air past the resistive heating element can be determined by a flow sensor, a pressure sensor, and/or one or more measured characteristics representative of air restriction of the vaporizer device. The target aerosol yield can be proportional to the flow rate. The target aerosol yield can be a function of the flow rate. The target aerosol yield can include a predetermined constant or a user-adjustable parameter. The user-adjustable parameter can include a desired output target based on a desired evaporation rate, a desired number of puffs, a particular time period, and/or a daily output target. The target aerosol yield can be adjusted to respond to one or more user behaviors of one or more users and/or one or more vaporizer devices. Controlling the power delivery to the resistive heating element can be further in response to an amount of power required to maintain a predefined temperature of the resistive heating element. Controlling the power delivery to the heating element can include selecting the power delivery such that the heating element temperature remains under a predetermined temperature. The predicting the amount of evaporation can include executing an algorithm using the received inputs.

In yet another aspect, a method includes receiving data characterizing a power delivery to a resistive heating element of a vaporizer device, a temperature of the resistive heating element, and/or a flow rate of air past the resistive heating element; predicting, using the received data, an amount of evaporation of vaporizable material located at the resistive heating element; and controlling the power delivery to the resistive heating element in response to the predicted amount of evaporation of the vaporizable material, the controlling including increasing or decreasing an instantaneous power delivery to the heating element such that a target aerosol yield is produced.

One or more of the following features can be included in any feasible combination. For example, the received data characterizing the flow rate of air past the resistive heating element can be determined by a flow sensor, a pressure sensor, and/or one or more measured characteristics representative of air restriction of the vaporizer device. The target aerosol yield can be proportional to the flow rate. The target aerosol yield can be a function of the flow rate. The target aerosol yield can include a predetermined constant or a user-adjustable parameter. The user-adjustable parameter can include a desired output target based on a desired evaporation rate, a desired number of puffs, a particular time period, and/or a daily output target. The target aerosol yield can be adjusted to respond to one or more user behaviors of one or more users and/or one or more vaporizer devices. Controlling the power delivery to the resistive heating element can be further in response to an amount of power required to maintain a predefined temperature of the resistive heating element. Controlling the power delivery to the heating element can include selecting the power delivery such that the heating element temperature remains under a predetermined temperature. The predicting the amount of evaporation can include executing an algorithm using the received data. The vaporizer device can include a resistive heating element and circuitry configured to control delivery of electrical power to the resistive heating element from a power source. The resistive heating element can be configured to provide heat to a vaporizable material to cause vaporization of the vaporizable material into a flowing air stream to form an entrained aerosol.

Implementations of the current subject matter can include, but are not limited to, methods consistent with the descriptions provided herein as well as articles that comprise a tangibly embodied machine-readable medium operable to cause one or more machines (e.g., computers, and the like) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g., the Internet, a wireless wide area network, a local area network, a wide area network, a wired network, or the like), via a direct connection between one or more of the multiple computing systems, and the like.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to a portable vaporizer device having a resistive heater and a battery or other mobile power source, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1A:
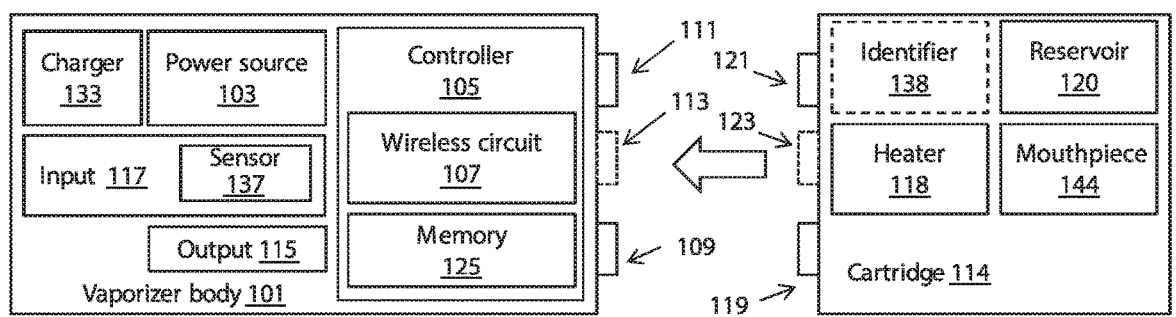
FIG. 1A shows a schematic diagram illustrating features of a vaporizer device having a cartridge and a vaporizer device body consistent with implementations of the current subject matter.

Implementations of the current subject matter relate to approaches for controlling an aerosol output rate provided by a vaporizer device. In some implementations, a controller implements a control law in which power delivery to a heater of the vaporizer device is controlled in response to a predicted amount of evaporation (e.g., aerosol yield measurement) of a vaporizable material. The controlling of the power delivery may include increasing or decreasing the power delivery to the heater such that a target aerosol yield (e.g., a controlled dose) is produced. The control law may adjust the mass output rate to respond to user behaviors.

Various approaches are available for controlling a vaporizer device. For example, a battery (or other power source, which can be portable or connected to the main power of a residential, commercial, or other building or the like) of the vaporizer device can be directly connected to a resistive heater such that full current draw from the battery (or other power source) is delivered whenever the resistive heater is turned on (e.g., by activation of a switch, and the like). The circuit providing current can be controlled to on (closed) or off (open) according to an algorithm or control law, and the like configured to determine when the resistive heater should be energized. In a simple example, the circuit can be closed (current flowing) when the temperature is below a set point and open (current not flowing) when the temperature is above the set point. In more sophisticated systems, current supplied may be more carefully regulated, for example using a proportional-integral-derivative (PID) control law, or the like.

A PID controller can include a control loop feedback mechanism suitable for continuously modulated control. A PID controller can continuously calculate an error value as the difference between a desired set point and a measured process variable. The PID controller can apply a correction based on proportional, integral, and derivative terms.

In other examples, voltage applied to the resistive heater may be regulated to a predetermined or user adjustable constant. In still other examples, power delivered to the heater may be regulated to a predetermined or user adjustable constant. In more sophisticated systems, a temperature to which the resistive heater heats may be controlled, for example, by measuring a temperature of the resistive heater using a thermal coefficient of resistance (TCR) based correlation or some other approach. A control law, such as a PID control algorithm, may be implemented to deliver a correct amount of power needed to hold the heater to a predetermined or user adjustable constant and/or to meet some other temperature condition, which need not be a constant temperature.

Such approaches generally do not include any quantification of or control over an amount of vaporizable material provided by the vaporizer device in aerosol form for inhalation by a user of the vaporizer device. In the context of the current disclosure, an "amount of vaporizable material" may be quantified in one or more of a variety of manners, including, for example, a mass delivered per unit time, a density or mass or unit volume of air flowing through the vaporizer as part of a user "puff," a total mass of the vaporizable material delivered per puff, and the like. Another way to characterize "an amount of vaporizable material" can include quantification of both a mass or a volume of air and a mass of vaporizable material entrained in that mass or volume of air such that a concentration of the vaporizable material in the air can be calculated.

Regardless of the control approach employed with a vaporizer device (e.g., uncontrolled or controlled by voltage, power, or temperature, or some combination thereof), the aerosol yield of the vaporizer device is generally dependent on a variety of uncontrollable parameters, such as the flow rate of air drawn by the user and the rate of liquid delivery to the heater. These non-constant variables can readily result in an inconsistent aerosol yield, which may be undesirable to the user.

Existing control approaches for vaporizer devices generally result in the aerosol yield (e.g., the mass of aerosol material produced per unit time) either decreasing or remaining constant as the flow rate induced by the user (e.g., an amount of air drawn through the vaporizer per unit time due to inhalation by the user on a mouthpiece of the vaporizer device) increases. This effect occurs because air flowing past the resistive heating element is heated by interaction with the resistive heating element, thereby drawing heat from the resistive heating element. Vaporization of the vaporizable material also removes heat from the resistive heating element in the form of latent heat of vaporization. If the vaporizer device includes a temperature control approach for maintaining the temperature of the resistive heating element at or below a certain temperature, at best, the rate of vaporization of the vaporizable material will be constant. For an aerosol yield per time that remains constant or decreases with increased air flow, the result will be an aerosol with decreasing particle density as flow rate increases. It may be more desirable to the user to have an aerosol of constant, or even increasing, particle density as the user puffs harder.

Implementations of the current subject matter relate to approaches for controlling an aerosol output rate provided by a vaporizer device. The aerosol output rate in this context can refer to either of a total mass of the vaporizable material delivered per unit time or, alternatively, a total mass of the vaporizable material delivered per "puff" (e.g., per a single inhalation drawn by the user on the vaporizer device). In the following description, unless specified and/or inconsistent with the context of the description, either of these metrics are applicable.

A vaporizer device with which implementations of the current subject matter can be employed can include a battery, a microcontroller, a printed circuit board (PCB), an electronic heater, a means of delivering vaporizable material to the heater, a method for measuring the temperature of the heater, a method for measuring flow through the vaporizer, and a method for measuring or predicting the instantaneous aerosol yield from the vaporizer FIGS. 1A-2C illustrate example vaporizer devices 100, 200 and features that may be included therein consistent with implementations of the current subject matter. It will be understood by one of ordinary skill in the art that various inventive features described herein or otherwise within the scope of the current subject matter may be implemented in differently configured vaporizers and that any structural descriptions of vaporizer features are not intended to be limiting except to the extent that they appear in the claims.

Figure 1B:
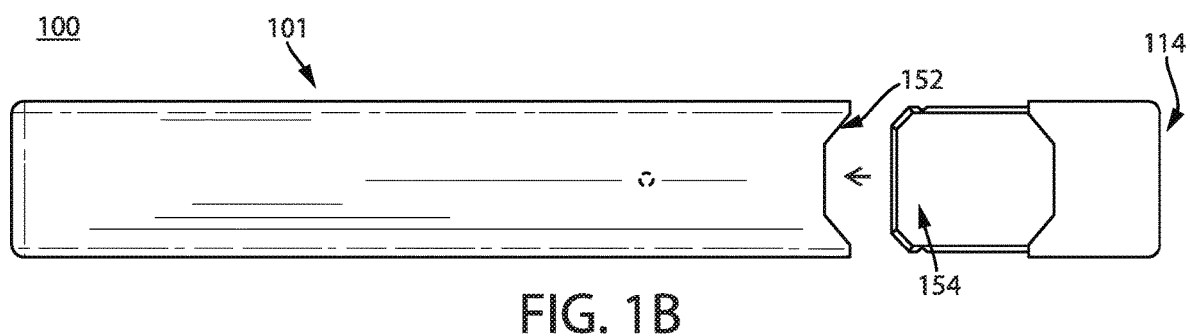
FIG. 1B shows a diagram providing a top view of a vaporizer device with a cartridge separated from a cartridge receptacle on a vaporizer device body consistent with implementations of the current subject matter.
Figure 1C:
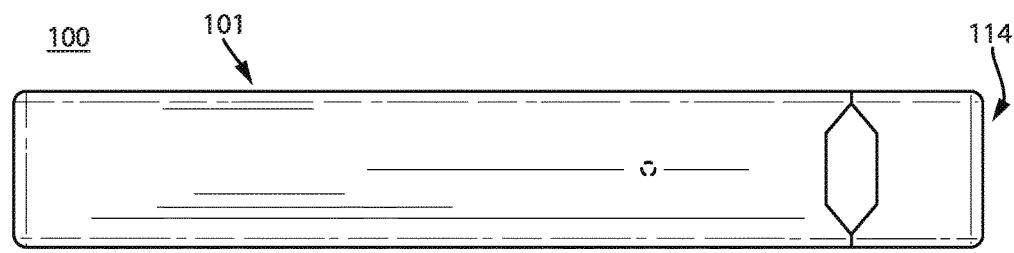
FIG. 1C shows a diagram providing a top view of a vaporizer device with a cartridge inserted into a cartridge receptacle on a vaporizer device body consistent with implementations of the current subject matter.
Figure 1D:
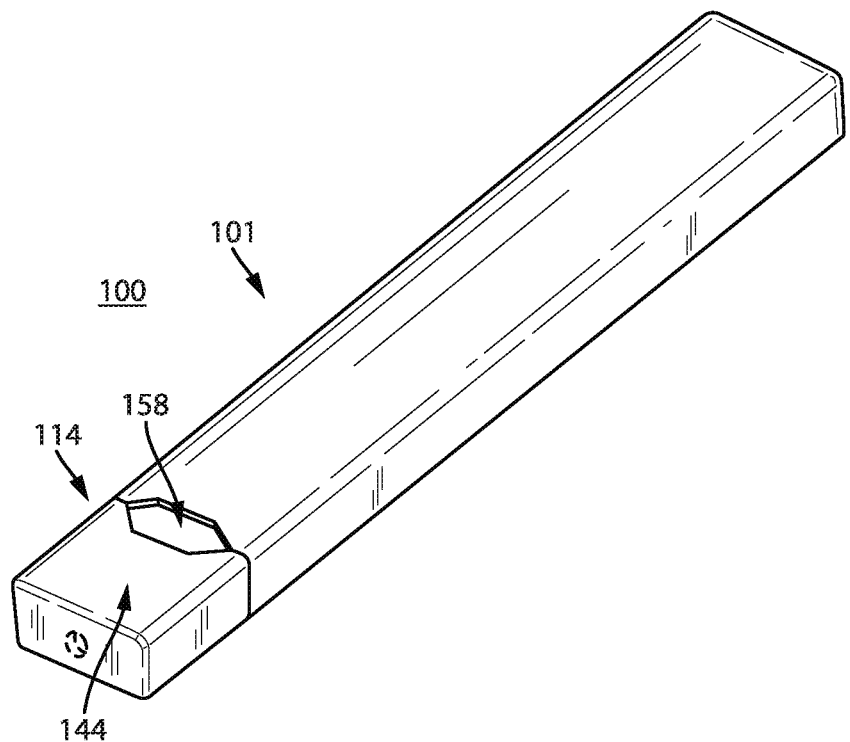
FIG. 1D shows a diagram providing a top isometric perspective view of a vaporizer device with a cartridge inserted into a cartridge receptacle on a vaporizer device body consistent with implementations of the current subject matter.
Figure 1E:
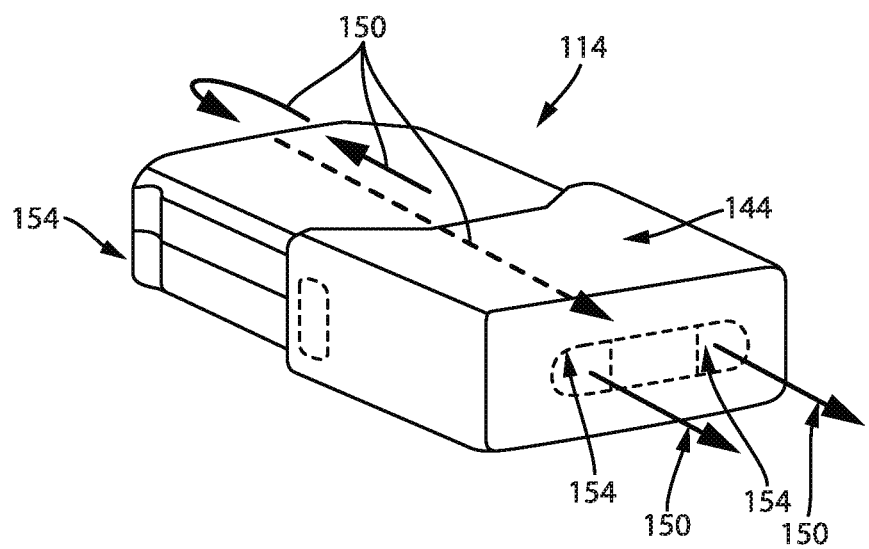
FIG. 1E shows a diagram providing a top isometric perspective view from a mouthpiece end of a cartridge suitable for use with a vaporizer device body consistent with implementations of the current subject matter.

FIG. 1A shows a schematic view of a vaporizer device 100 that includes a cartridge, and FIGS. 1B-1E show views of an exemplary vaporizer device 100 with a vaporizer device body 101 and a cartridge 114. FIGS. 1B and 1C show top views before and after connecting a cartridge 114 to a vaporizer device body 101. FIG. 1D shows an isometric perspective view of the vaporizer device 100, which includes a vaporizer device body 101 combined with a cartridge 114, and FIG. 1E shows an isometric perspective view of one variation of a cartridge 114 holding a liquid vaporizable material. In general, when a vaporizer device includes a cartridge (such as the cartridge 114), the cartridge 114 may include one or more reservoirs 120 configured to contain a vaporizable material. Any appropriate vaporizable material may be contained within the reservoir 120 of the cartridge 114, including solutions of nicotine or other organic materials as well as compositions that may include one or more neat (e.g., not dissolved in a solvent) chemical compounds, mixtures, formulations, and the like.

As noted above, the vaporizer device 100 shown in FIG. 1 includes a vaporizer device body 101. As shown in FIG. 1, a vaporizer device body 101 consistent with implementations of the current subject matter may include a power source 103 (e.g., a device or system that stores electrical energy for on-demand use), which may be a battery, capacitor, a combination thereof, or the like, and which may be rechargeable or non-rechargeable. A controller 105, which may include a processor (e.g., a programmable processor, special purpose circuitry, or the like), can also be included as part of the vaporizer device body 101. The vaporizer device body 101 may include a housing that encloses one or more of the components of the vaporizer body, such as the power source 103, the controller 105, and/or any of the other components described herein as being part of such a device. In various implementations of a vaporizer device that includes a vaporizer device body 101 and a cartridge 114, the cartridge 114 may be attached on, in, or partially in the vaporizer device body 101. For example, the vaporizer device body 101 may include a cartridge receptacle into which the cartridge 114 may be insertably received.

A processor of the controller 105 may include circuitry to control operation of a heater 118, which can optionally include one or more heating elements for vaporizing a vaporizable material contained within the cartridge 114, for example within a reservoir or container that is part of the cartridge 114. In various implementations, the heater 118 may be present in the vaporizer device body 101 or within the cartridge 114 (as shown in FIG. 1A), or both. The controller circuitry may include one or more clocks (oscillators), charging circuitry, I/O controllers, memory, and the like. Alternatively or in addition, the controller circuitry may include circuitry for one or more wireless communication modes, including Bluetooth, near-field communication (NFC), WiFi, ultrasound, ZigBee, RFID, and the like. The vaporizer device body 101 may also include a memory 125 that may be part of the controller 105 or otherwise in data communication with the controller. The memory 125 may include volatile (e.g., random access memory) and/or nonvolatile (e.g., read-only memory, flash memory, solid state storage, a hard drive, other magnetic storage, and the like) memory or data storage.

Further with reference to FIG. 1, a vaporizer device 100 may include a charger 133 (and charging circuitry which may be controlled by the controller 105), optionally including an inductive charger and/or a plug-in charger. For example, a universal serial bus (USB) connection may be used to charge the vaporizer device 100 and/or to allow communication over a wired connection between a computing device and the controller 105. The charger 133 may charge the onboard power source 103. A vaporizer 100 consistent with implementations of the current subject matter may also include one or more inputs 117, such as buttons, dials, or the like, a sensor 137, which may include one or more sensors such as accelerometers or other motion sensors, pressure sensors (e.g., relative and/or absolute pressure sensors, which may be capacitive, semiconductor-based, and the like.), flow sensors, or the like. One more such sensors 137 may be used by the vaporizer 100 to detect user handling and interaction. For example, detection of a rapid movement (such as a shaking motion) of the vaporizer 100 may be interpreted by the controller 105 (e.g., through receipt of a signal from one or more of the sensors 137) as a user command to begin communication with a user device that is part of a vaporizer system and that can be used for controlling one or more operations and/or parameters of the vaporizer 100 as described in more detail below. Additionally or alternatively, detection of a rapid movement (such as a shaking motion) of the vaporizer 100 may be interpreted by the controller 105 (e.g., through receipt of a signal from one or more of the sensors 137) as a user command to cycle through a plurality of temperature settings to which the vaporizable material held within the cartridge 114 is to be heated by action of the heater 118. In some optional variations, detection of removal of the cartridge 114 by the controller 105 (e.g., through receipt of a signal from one or more of the sensors 137) during a cycling-through of the plurality of temperature settings may act to establish the temperature (e.g., when the cycle is at a desired temperature, a user may remove the cartridge 114 to set the desired temperature). The cartridge 114 may then be re-engaged with the vaporizer device body 101 by the user to allow use of the vaporizer 100 with the heater controlled by the controller 105 consistent with the selected temperature setting. The plurality of temperature settings may be indicated through one or more indicators on the vaporizer device body 101. A pressure sensor can, as noted above, be used in detection of any of a start, an end, or a continuation of a puff.

A vaporizer device 100 consistent with implementations of the current subject matter may also include one or more outputs 115. Outputs 115 as used herein can refer to any of optical (e.g., LEDs, displays, and the like), tactile (e.g., vibrational, and the like), or sonic (e.g., piezoelectric, and the like) feedback components, or the like, or some combination thereof.

A vaporizer device 100 consistent with implementations of the current subject that includes a cartridge 114 may include one or more electrical contacts (e.g., pins, plates, sockets, mating receptacles or other features for coupling electrically with other contacts, and the like), such as the vaporizer device body electrical contacts 109, 111, 113 shown in FIG. 1A) on or within the vaporizer device body 101 that may engage complementary cartridge contacts 119, 121, 123 (e.g., pins, plates, sockets, mating receptacles or other features for coupling electrically with other contacts, and the like) on the cartridge 114 when the cartridge is engaged with the vaporizer device body 101. The contacts on the vaporizer body 101 are generally referred to herein as "vaporizer body contacts" and those on the cartridge 114 are generally referred herein to as "cartridge contacts." These contacts may be used to provide energy from the power source 103 to the heater 118 in implementations of the current subject matter in which the heater 118 is included in the cartridge 114. For example, when the cartridge contacts and the vaporizer body contacts are respectively engaged by coupling of the cartridge 114 with the vaporizer device body 101, an electrical circuit can be formed allowing control of power flow from the power source 103 in the vaporizer device body 101 to the heater 118 in the cartridge 114. A controller 105 in the vaporizer device body 101 can regulate this power flow to control a temperature at which the heater 118 heats a vaporizable material contained in the cartridge 114.

While three vaporizer device body contacts 109, 111, 113 and three cartridge contacts 119, 121, 123 are shown, certain implementations of the current subject matter may use only two of each type of contacts to complete an electrical circuit that can be used for power delivery from the power source 103 to the heater 118 and optionally also for measuring a temperature of a heating element in the heater (e.g., by briefly and intermittently interrupting a flow of current to the heating element, measuring a resistance of the heating element during these brief interruptions, and using a thermal resistance coefficient to obtain temperature from the measured resistance) and/or transmitting data between the optional identifier 138 and the controller 105. Alternatively or in addition, additional contacts (e.g., optional contacts 113 and 123) may be included for data passing, temperature measurements, pressure sensor measurements (e.g., if a pressure sensor is included on the cartridge while the controller 105 is in the vaporizer device body 101).

An airflow path (150, in FIG. 1E) can direct air to the heater, where the air is combined with vaporized vaporizable material from a reservoir 120 such that an inhalable aerosol is generated for delivery to a user via a mouthpiece 144, which can also be part of the cartridge 114. The airflow path 150 may, in some examples, pass between an outer surface of the cartridge 114 and an inner surface of a cartridge receptacle on the vaporizer device body 101 as described further below.

Any compatible electrical contact may be used, including pins (e.g., pogo pins), plates, and the like. In addition, as described below, in some implementations of the current subject matter one-way or two-way communication is provided between the vaporizer device body 101 and the cartridge 114 through one or more electrical contacts, which may include the electrical contacts used to provide energy from the power source 103 to the heater 118, which may include a heating element such as a resistive heating element. The cartridge 114 and the vaporizer device body 101 may be removably coupled together, e.g., by engaging a portion of a housing of the cartridge 114 with the vaporizer device body 101 and/or the vaporizer housing in a mechanical connection (e.g., a snap and/or friction fit). Alternatively or additionally, the cartridge 114 and the vaporizer device body 101 may be coupled magnetically or via some other coupling or engaging mechanism. Other connection types are also within the scope of the current subject matter, as are combinations of two or more connection types.

Figure 1F:
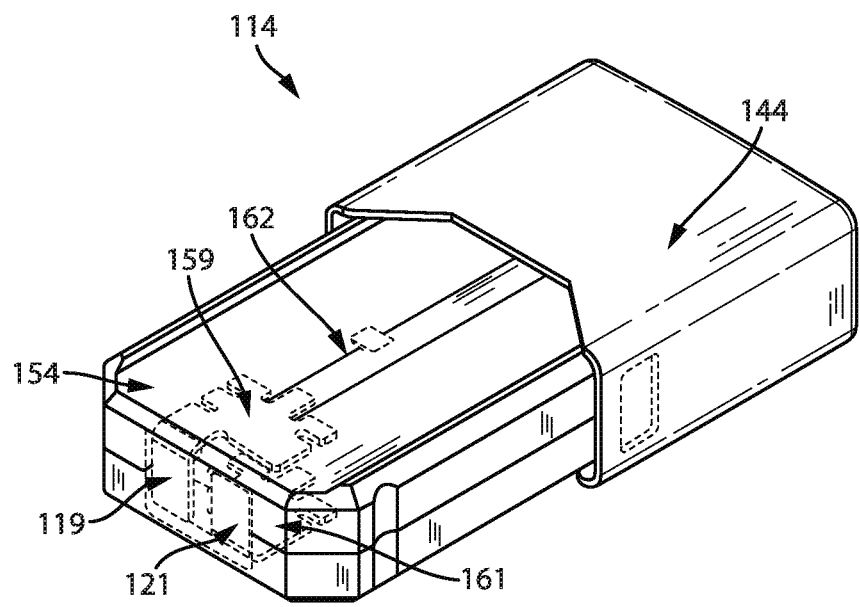
FIG. 1F shows a diagram providing a top isometric perspective view from an opposite end of a cartridge suitable for use with a vaporizer device body consistent with implementations of the current subject matter.

FIGS. 1B to 1F illustrate an example of a vaporizer 100 with a vaporizer device body 101 and cartridge 114. The two are shown unconnected in FIG. 1B and connected in FIG. 1C. FIG. 1D shows an isometric perspective view of the combined vaporizer device body 101 and cartridge 114, and FIG. 1E and FIG. 1F shows an individual cartridge 114 from two different views. FIGS. 1B-1F in combination illustrate an example cartridge-based vaporizer device including many of the features generally shown in FIG. 1A. Other configurations, including some or all of the features described herein, are also within the scope of the current subject matter. FIG. 1D shows a vaporizer device 100 having a cartridge 114 coupled into a cartridge receptacle of the vaporizer device body. In addition to the part 154 of the cartridge 114 that is insertably received and thereby obscured from view in the cartridge receptacle 152, the cartridge 114 and/or vaporizer device body 101 can also include a feature that allows some part 158 of the cartridge 114 to be visible when the cartridge 114 that is insertably received in the cartridge receptacle 152. This part 158 of the cartridge that remains visible can include a surface that is clear, translucent, or the like through which at least a level of the vaporizable material within a reservoir 120 of the cartridge 114 can be discerned.

FIG. 1E also illustrates an example of an airflow path 150 for air to be drawn by a user puff from outside of the cartridge 114 past the heater 118 (e.g., through a vaporization chamber that includes or contains the heater 118), and on to the mouthpiece 144 for delivery of the inhalable aerosol. The mouthpiece may optionally have multiple openings through which the inhalable aerosol is delivered. For example, a cartridge receptacle 152 may be present at one end of a vaporizer device body 101, such that an insertable end 154 of the cartridge 114 may be insertably received into the cartridge receptacle 152. When the cartridge insertable part 154 is fully inserted into the cartridge receptacle 152, an inner surface of the cartridge receptacle 152 forms one surface of part of the airflow path 150 and an exterior surface of the cartridge insertable part 154 form another surface of that part of the airflow path.

As shown in FIG. 1E, this configuration causes air to flow down around the cartridge insertable part 154 into the cartridge receptacle 152 and then back in the opposite direction after passing around the inserted end (e.g., an end opposite an end that includes the mouthpiece 144) of the cartridge 114 as it enters into the cartridge body toward the vaporization chamber and heater 118. The airflow path 150 then travels through the interior of the cartridge 114, for example via one or more tubes or internal channels to one or more outlets 156 formed in the mouthpiece 144. For a cartridge having a non-cylindrical shape 144, the mouthpiece 114 may likewise be non-cylindrical, and more than one outlets 156 may be formed in the mouthpiece, optionally arranged in a line along a longer of two transverse axes of the cartridge 114, where a longitudinal axis of the cartridge is oriented along a direction the cartridge 114 is moved to be insertably received or otherwise coupled to the vaporizer device body 101 and the two transverse axes are perpendicular to each other and to the longitudinal axis.

FIG. 1F shows additional features that may be included in a cartridge 114 consistent with the current subject matter. For example, the cartridge 114 can include two cartridge contacts 119, 121 disposed on the insertable part 154, which is configured to be inserted into the cartridge receptacle 152 of a vaporizer device body 101. These cartridge contacts 119, 121 can optionally each be part of a single piece of metal that forms a conductive structure 159, 161 connected to one of two ends of a resistive heating element. The two conductive structures can optionally form opposing sides of a heating chamber and can also act as heat shields and/or heat sinks to reduce transmission of heat to outer walls of the cartridge 114. FIG. 1F also shows a central tube 162 within the cartridge 114 that defines part of the airflow path 150 between the heating chamber formed between the two conductive structures 159, 161 and the mouthpiece 144.

As mentioned above, the cartridge 114 and optionally the vaporizer device body 101 may optionally be non-circular in cross section, with various oblong (e.g., one of two transverse axes which are orthogonal to a longitudinal axis of the vaporizer device 100 being longer than the other) cross-sectional shapes contemplated, including approximately rectangular, approximately rhomboidal, approximately triangular or trapezoidal, approximately oval in shape, and the like. It will be well understood by one of ordinary skill in the art that the use of "approximately" in this context contemplates that any vertices of the cross-sectional shape need not be sharp, but can instead have a non-zero radius of curvature, and that any surfaces between such vertices need not be completely planar but can instead have a non-infinite radius of curvature.

Figure 2A:
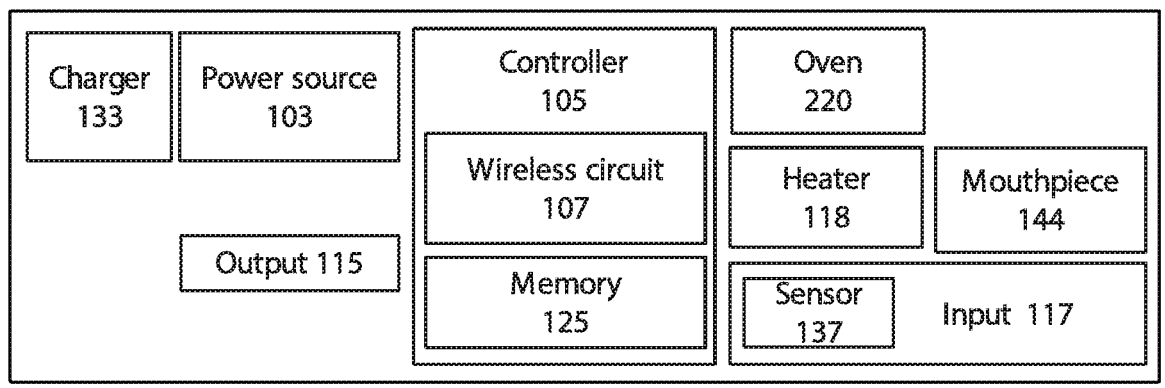
FIG. 2A shows a schematic diagram illustrating features of a non-cartridge-based vaporizer device consistent with implementations of the current subject matter.
Figure 2B:
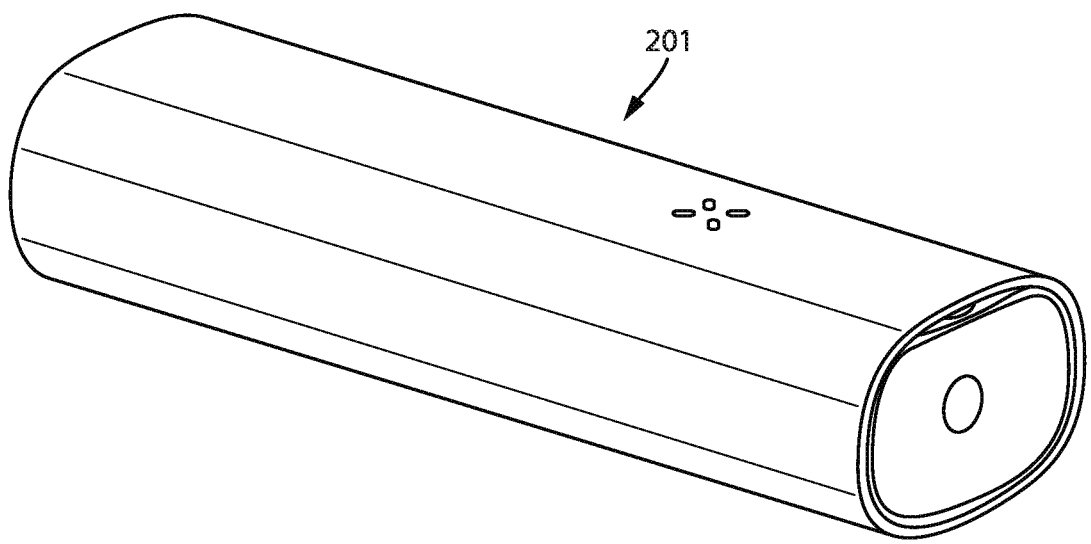
FIG. 2B shows a diagram providing a side isometric perspective view of a non-cartridge-based vaporizer device.
Figure 2C:
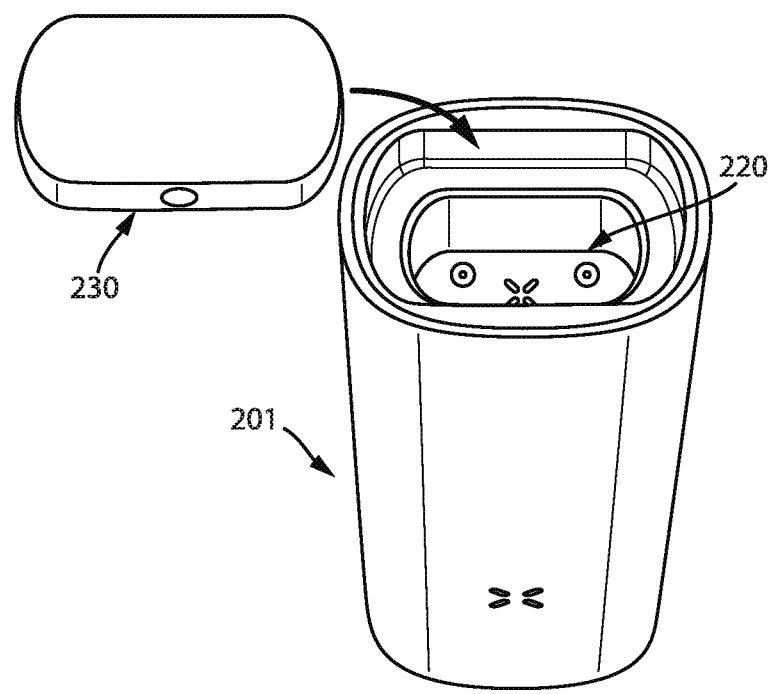
FIG. 2C shows a diagram providing a bottom isometric perspective view of the non-cartridge-based vaporizer device.

FIGS. 2A-2C relate to an example implementation of the current subject matter in which the vaporizer device is not cartridge based. FIG. 2A shows a schematic diagram of a vaporizer device 200 that does not use a cartridge (but may still optionally accept a cartridge), but may instead (or additionally) be configured for use with a loose-leaf material or some other vaporizable material (e.g., a solid, a wax, and the like). The vaporizer device 200 in FIG. 2A may be configured to receive, in an oven 220 (e.g., a vaporization chamber), a vaporizable material such as a loose vaporizable material, a wax, and/or some other liquid or solid vaporizable material. Many elements similar to those present in the vaporizer device 100 using a cartridge 114 shown in FIG. 1A-1E may also be included as part of a vaporizer device 200 that does not require use of cartridges. For example, a vaporizer device 200 may include, in one housing, control circuitry 105 which may include power control circuitry, and/or wireless circuitry 207, and/or memory 125. A power source 103 (e.g., a battery, capacitor, and the like) within the housing may be charged by a charger 133 (and may include charging control circuitry, not shown). The vaporizer device 200 may also include one or more outputs 115 and one or more inputs 117 with sensors 137, which may include one or more of the sensors discussed above in regards to the cartridge-based vaporizer device 100. In addition, the vaporizer device 200 may include one or more heaters 118 that heat a vaporization chamber, which may be an oven 220 or other heating chamber. The heater 118 may be controlled using the resistance of the heater 118 to determine the temperature of the heater, e.g., by using the temperature coefficient of resistivity for the heater. A mouthpiece 144 may also be included in such a vaporizer device 200 for delivery of a generated inhalable aerosol to a user. FIG. 2B shows a side isometric perspective of an exemplary vaporizer device 200 with a vaporizer device body 101. In the bottom isometric perspective view of FIG. 2C, a lid 230 is shown removed from the vaporizer body 201, exposing the oven/vaporization chamber 220.

The current subject matter can apply to vaporizer devices that heat materials having origin as plant leaves or other plant components in order to extract plant specific flavor aromatics and other products as vapor. These plant materials may be chopped and blended into a homogenized construct with a variety of plant products that may include tobacco, in which case nicotine and/or nicotine compounds may be produced and delivered in aerosol form to the user of such a vaporizer device. The homogenized construct may also include vaporizable liquids such as propylene glycol and glycerol in order to enhance the vapor density and aerosol produced when heated. In order to avoid production of unwanted harmful or potentially harmful constituents (HPHCs) vaporizer devices can include heaters having temperature control. Such vaporizer devices that heat plant leaves or homogenized construct as described above such that temperatures are kept below combustion levels are generally referred to as heat not burn (HNB) devices.

Figure 3:
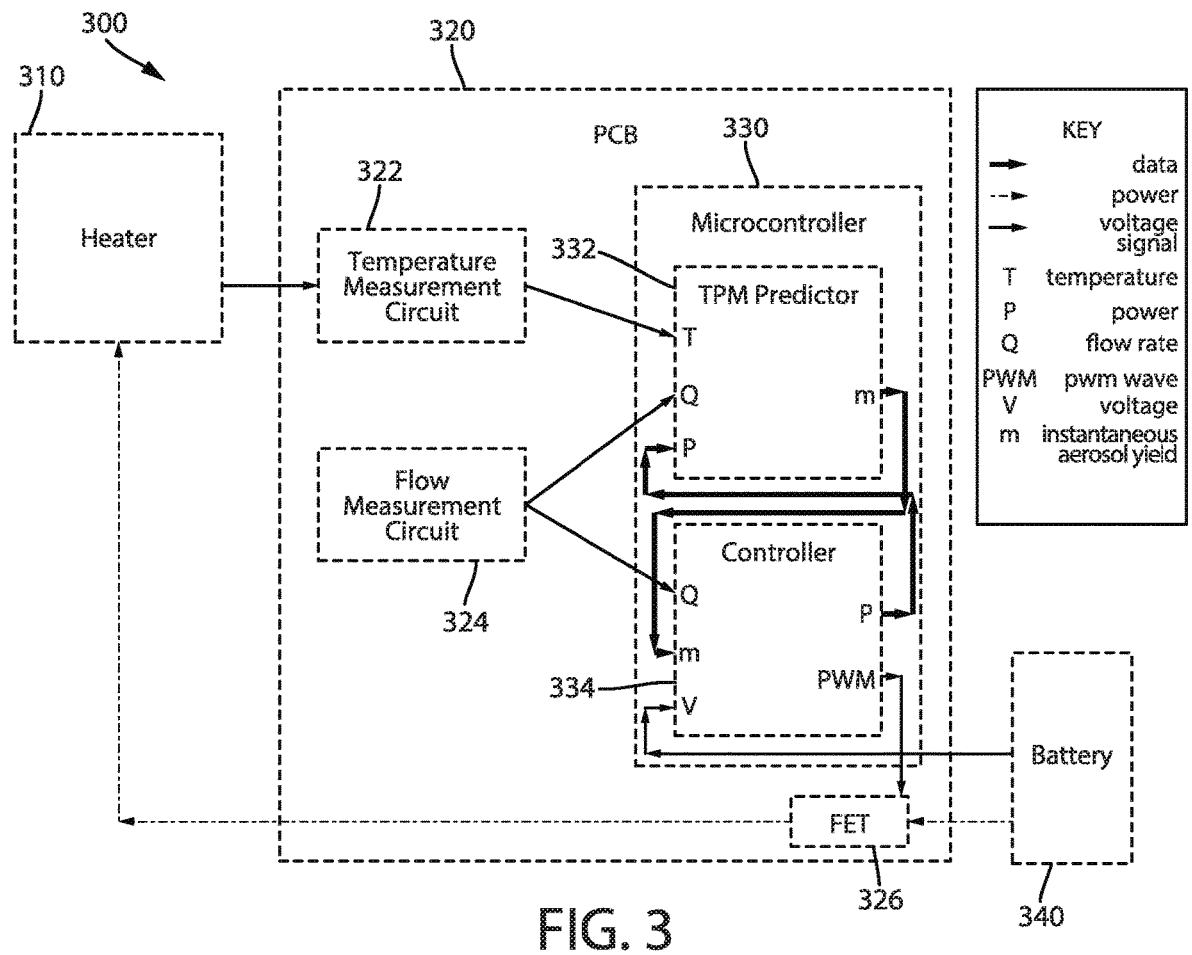
FIG. 3 shows a diagram illustrating aspects of a system with features consistent with implementations of the current subject matter.

FIG. 3 shows a block diagram representation of a system 300 for controlling an aerosol output rate provided by a vaporizer device, consistent with implementations of the current subject matter described herein. The system 300 includes a heater 310 (e.g., resistive heating element), circuitry 320, and a battery 340 (or other power source). The circuitry 320 (e.g., a printed circuit board) may include a temperature measurement circuit 322 for measuring temperature of the heater 310, a flow measurement circuit 324 for measuring a flow rate in an air flow path of the vaporizer device, and a FET 326 to amplify the power signal from the controller 334 to the heater 310.

In some implementations of the current subject matter, the temperature measurement circuit 322 may implement a TCR correlated resistance measurement to measure a temperature of the heater 310. In other implementations, the temperature measurement circuit 322 may incorporate a thermistor, a thermocouple, and/or an infrared (IR) sensor for measuring temperature of the heater 310.

In some implementations of the current subject matter, the flow measurement circuit 324 may include a flow sensor in an air flow path of a vaporizer to measure flow rate in the air flow path in which the heater 310 is positioned. In other implementations, flow rate can be measured with various types of pressure sensors, such as an absolute pressure sensor, a relative pressure sensor, a hot wire anemometer, and/or a paddlewheel. In some instances, a pressure sensor with a well-defined and known air restriction can be used to estimate flow rate. In other instances, air restriction of the vaporizer device and/or other known or measureable characteristics can be calculated and used to determine or estimate flow rate. In other embodiments, a flow rate measurement or estimation is not required. For example, a flow rate is not necessary for determining a total mass of vaporizable material delivered in a given puff or over time, but may be necessary for calculation of a concentration of inhalable aerosol in a given volume of air.

In some implementations of the current subject matter, an instantaneous aerosol yield from the vaporizer device may be determined and/or predicted by an algorithm that uses as inputs power, temperature of the heater 310, and/or flow measurements of a flow rate of air past the heater 310 for predicting the rate of evaporation at the heater. Alternatively, the instantaneous aerosol yield from the vaporizer can be measured and/or predicted by measuring and/or predicting the amount of material evaporated by the heater during a short sample period (e.g., <100 ms).

With continued reference to FIG. 3, the microcontroller 330 includes an aerosol yield predictor 332 and a controller 334. The predictor 332 uses the received inputs representative of a power delivery to the heater 310, a temperature of the heater 310 (from the temperature measurement circuit 312), and/or a flow rate of air past the heater 310 (from the flow measurement circuit 324) to predict an amount of evaporation of the vaporizable material at the heater 310.

The controller 334 implements a control law in which the power delivery to the heater 310 is controlled in response to the predicted amount of evaporation of the vaporizable material (as predicted by the predictor circuit 332). In some implementations, the controlling of the power delivery includes increasing or decreasing the power delivery to the heater 310 such that a target aerosol yield is produced.

The control law uses the aerosol yield measurement (e.g., the predicted amount of evaporation of the vaporizable material from the predictor 332) as a control signal to attenuate the amount of power delivered to the heater 310. The controller 334 may set the control target for instantaneous aerosol yield proportional to the flow rate as measured by a flow sensor (e.g., the flow measurement circuit 314). The control target may alternatively be set as a constant or a user adjustable parameter. The control target for instantaneous aerosol may be adjusted over the course of a puff, over the course of successive puffs, or in response to other user behaviors, preferences, and/or goals. For example, a user may set one or more of the following as a desired output target: a desired evaporation rate (such as 1 mg/s), a desired number of puffs per a particular time period, and/or a particular program to achieve a daily goal (e.g., a specific target in the morning and another target in the evening, and the like). In accordance with implementations of the current subject matter, the control law may be implemented as part of a feed-back loop to control electrical power delivery to the heater to achieve a desired (e.g., set point, threshold, target, and the like) mass output rate, which may or may not be user configurable.

Additionally, a vaporizer device that implements the control law in accordance with specific implementations described herein may accordingly adjust the mass output rate to respond to user behaviors (for example, by utilizing a sample of users and history of one or more devices). Thus, the mass output rate may be automatically adjusted depending on time of day, day of week, and the like In some implementations, in addition to the mass output control law, a temperature control law may be implemented in tandem. The mass output control law, as described herein, dictates the amount of power to achieve a constant mass output. A temperature control law determines the amount of power to maintain a temperature. In accordance with some implementations, the lesser value of power is supplied to the heater to avoid risk of going over a certain temperature. This serves as a safeguard feature by ensuring a certain, predefined temperature is not exceeded.

Figure 4:
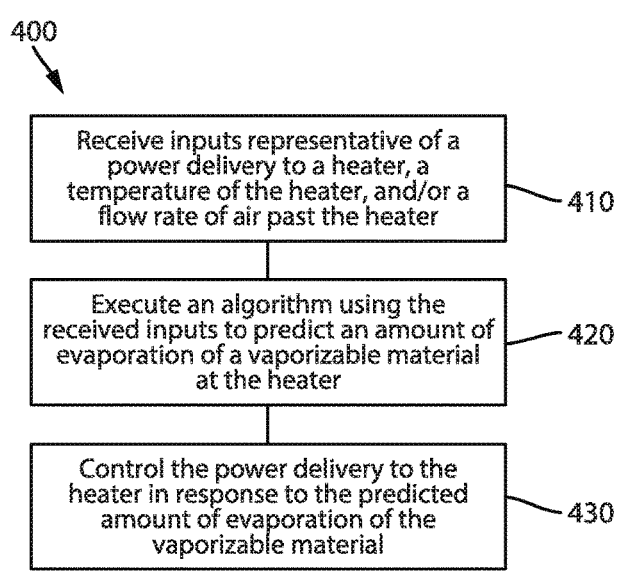
FIG. 4 shows a process flow diagram illustrating aspects of a method having one or more features consistent with implementations of the current subject matter.

With reference to FIG. 4, a process flow chart 400 illustrates features of a method, which may optionally include some or all of the following. At 410, inputs are received, the inputs representative of a power delivery to a heater 310, a temperature of the heater 310, and/or a flow rate of air past the heater 310.

At 420, an algorithm using the received inputs is executed to predict an amount of evaporation of a vaporizable material at the heater. For example, predicting the amount of evaporation of the vaporizable material at the heater can include determining an amount of vapor and/or a material in the vapor based on the electrical and thermal properties (e.g., power or energy applied to the heating element and the temperature of the material immediately before and as it is vaporized). Other approaches are possible.

At 430, the power delivery to the heater is controlled in response to the predicted amount of evaporation of the vaporizable material. For example, the controlling of the power delivery may include increasing or decreasing an instantaneous power delivery to the heater 310 such that a target aerosol yield (e.g., a desired output rate) is produced. In some implementations, power delivery can be modulated by Pulse Width Modulating (PWM) current from the power source (e.g., battery) into the heater. The amount of power to deliver can be determined by a Proportional-Integral-Derivative (PID) control law. For example, a target mass evaporation rate set point (e.g., a target aerosol yield) can be predefined, for example, can be contained in memory. An error between the target mass evaporation rate (e.g., a target aerosol yield) and the predicted amount of evaporation can be computed, for example, by taking a difference between the target and predicted amount of evaporation. The power can be adjusted based on one or more of: a function of the error; a sum of a history of errors from previous predictions (e.g., iterations); and/or a change in error from the previous prediction to the current prediction. Additional approaches to modulating power and additional control laws can be used in some implementations to control the amount of power delivered to an appropriate amount of power.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A vaporizer device comprising:
a resistive heating element;
circuitry configured to control delivery of electrical power to the resistive heating element from a power source, the resistive heating element configured to provide heat to a vaporizable material to cause vaporization of the vaporizable material into a flowing air stream to form an entrained aerosol; and
a controller configured to perform operations comprising:
receiving inputs representative of a power delivery to the resistive heating element, a temperature of the resistive heating element, and a flow rate of air past the resistive heating element, wherein the received input representative of the flow rate of air past the resistive heating element is determined at least based on one or more measured characteristics representative of air restriction of the vaporizer device;

predicting, using the received inputs, an amount of evaporation of the vaporizable material at the resistive heating element; and controlling the power delivery to the resistive heating element in response to the predicted amount of evaporation of the vaporizable material, the controlling including increasing or decreasing an instantaneous power delivery to the heating element such that a target aerosol yield is produced.

2. The vaporizer device of claim 1, wherein the target aerosol yield is proportional to the flow rate.

3. The vaporizer device of claim 1, wherein the target aerosol yield is a function of the flow rate.

4. The vaporizer device of claim 1, wherein the target aerosol yield comprises a predetermined constant or a user-adjustable parameter.

5. The vaporizer device of claim 4, wherein the user-adjustable parameter comprises a desired output target based on a desired evaporation rate, a desired number of puffs, a particular time period, and/or a daily output target.

6. The vaporizer device of claim 1, wherein the target aerosol yield is adjusted to respond to one or more user behaviors of one or more users and/or one or more vaporizer devices.

7. The vaporizer device of claim 1, wherein controlling the power delivery to the resistive heating element is further in response to an amount of power required to maintain a predefined temperature of the resistive heating element.

8. The vaporizer device of claim 1, wherein controlling the power delivery to the heating element includes selecting the power delivery such that the heating element temperature remains under a predetermined temperature.

9. The vaporizer device of claim 1, wherein the predicting the amount of evaporation includes executing an algorithm using the received inputs.

10. A vaporizer device comprising:
a resistive heating element;
circuitry configured to control delivery of electrical power to the resistive heating element from a power source, the resistive heating element configured to provide heat to a vaporizable material to cause vaporization of the vaporizable material; and
a controller configured to perform operations comprising:
receiving at least one input, wherein one of the at least one input is representative of a flow rate of air past the resistive heating element that is determined at least based on one or more measured characteristics representative of air restriction of the vaporizer device;

predicting, using the at least one received input, an amount of evaporation of the vaporizable material at the resistive heating element; and controlling the power delivery to the resistive heating element in response to the predicted amount of evaporation of the vaporizable material, the controlling including increasing or decreasing an instantaneous power delivery to the heating element such that a target aerosol yield is produced.

11. The vaporizer device of claim 10, wherein another one of the at least one input is a power delivery to the resistive heating element or a temperature of the resistive heating element.

12. The vaporizer device of claim 10, wherein the received input representative of the flow rate of air past the resistive heating element is further determined by at least one of a flow sensor or a pressure sensor.

13. The vaporizer device of claim 10, wherein the target aerosol yield is proportional to the flow rate.

14. The vaporizer device of claim 10, wherein the target aerosol yield is a function of the flow rate.

15. The vaporizer device of claim 10, wherein the target aerosol yield comprises a predetermined constant or a user-adjustable parameter.

16. The vaporizer device of claim 15, wherein the user-adjustable parameter comprises a desired output target based on a desired evaporation rate, a desired number of puffs, a particular time period, and/or a daily output target.

17. The vaporizer device of claim 10, wherein the target aerosol yield is adjusted to respond to one or more user behaviors of one or more users and/or one or more vaporizer devices.

18. The vaporizer device of claim 10, wherein controlling the power delivery to the resistive heating element is further in response to an amount of power required to maintain a predefined temperature of the resistive heating element.

19. The vaporizer device of claim 10, wherein controlling the power delivery to the heating element includes selecting the power delivery such that the heating element temperature remains under a predetermined temperature.

20. The vaporizer device of claim 10, wherein the predicting the amount of evaporation includes executing an algorithm using the received inputs.

* * * * *